United States Patent
Toivonen et al.

(10) Patent No.: US 10,918,908 B2
(45) Date of Patent: Feb. 16, 2021

(54) METHOD, AN APPARATUS AND A SOFTWARE PRODUCT FOR PROVIDING A TRAINING PROGRAM

(71) Applicant: Firstbeat Analytics Oy, Jyväskylä (FI)

(72) Inventors: Johanna Toivonen, Jyväskylä (FI); Kaisa Hämäläinen, Jyväskylä (FI); Maunu Toiviainen, Jyväskylä (FI); Mikko Seppänen, Jyväskylä (FI); Joonas Korhonen, Jyväskylä (FI)

(73) Assignee: Firstbeat Analytics, Oy

( * ) Notice: Subject to any disclaimer, the term of this patent is extended or adjusted under 35 U.S.C. 154(b) by 64 days.

(21) Appl. No.: 16/216,398

(22) Filed: Dec. 11, 2018

(65) Prior Publication Data
US 2020/0179757 A1   Jun. 11, 2020

(51) Int. Cl.
*A63B 24/00* (2006.01)

(52) U.S. Cl.
CPC ...... *A63B 24/0062* (2013.01); *A63B 24/0075* (2013.01); *A63B 24/0087* (2013.01); *A63B 2024/0065* (2013.01); *A63B 2024/0068* (2013.01); *A63B 2024/0093* (2013.01)

(58) Field of Classification Search
CPC ............ A63B 24/0062; A63B 24/0075; A63B 24/0087; A63B 2024/0065; A63B 2024/0068; A63B 2024/0093
See application file for complete search history.

(56) References Cited

U.S. PATENT DOCUMENTS

| | | | |
|---|---|---|---|
| 7,717,827 B2 * | 5/2010 | Kurunmaki | A63B 24/0062 482/8 |
| 7,805,186 B2 | 9/2010 | Pulkkinen et al. | |
| 8,052,580 B2 * | 11/2011 | Saalasti | A61B 5/1112 482/8 |
| 8,465,397 B2 | 6/2013 | Saalasti et al. | |
| 9,237,868 B2 | 1/2016 | Seppanen et al. | |
| 9,468,807 B1 * | 10/2016 | Krueger | A63B 24/0075 |
| 9,697,740 B2 * | 7/2017 | Zhang | G09B 19/003 |
| 10,123,730 B2 | 11/2018 | Saalasti et al. | |
| 10,223,931 B1 * | 3/2019 | Clark | G09B 19/003 |
| 10,255,823 B2 * | 4/2019 | Jang | A63B 24/0075 |
| 10,413,779 B2 * | 9/2019 | Ingram | A63B 24/0059 |
| 10,540,483 B2 * | 1/2020 | Hardee | G16H 40/63 |
| 10,589,150 B2 * | 3/2020 | Ackland | A61B 5/14552 |

(Continued)

Primary Examiner — Joshua Lee
(74) Attorney, Agent, or Firm — Samuel M. Korte; Max M. Ali

(57) ABSTRACT

The application presents providing next workout recommendation(s) for a user. The current training load for the next workout recommendation is determined based on a present activity class, a phase of the micro-cycle of successive training days and the sum of the training load values for a number of past trainings. The present activity class of the user corresponds to a present fitness level of the user. A total target training load is determined based on the present activity class and the training goal, which relates to maintaining, increasing or increasing fast the fitness level of the user. The phase of the micro-cycle of successive training days for the next workout recommendation is determined by the realized training load value(s) for daily training session (s) of at least one previous day from training history data, as a percentage of the sum of the training load values for a number of past trainings.

20 Claims, 5 Drawing Sheets

(56) References Cited

U.S. PATENT DOCUMENTS

| | | | |
|---|---|---|---|
| 2006/0228681 A1* | 10/2006 | Clarke | A63B 24/00 434/236 |
| 2010/0216601 A1* | 8/2010 | Saalasti | A61B 5/1112 482/8 |
| 2011/0281249 A1* | 11/2011 | Gammell | G16H 10/20 434/247 |
| 2013/0172764 A1* | 7/2013 | Buckley | A61B 5/0205 600/509 |
| 2013/0325404 A1* | 12/2013 | Yuen | G06F 11/00 702/182 |
| 2015/0087478 A1* | 3/2015 | Zhang | A63B 24/0003 482/8 |
| 2016/0184637 A1 | 6/2016 | Pulkkinen et al. | |
| 2016/0220867 A1* | 8/2016 | Flaherty | G16H 20/30 |
| 2016/0263439 A1* | 9/2016 | Ackland | A61B 5/4866 |
| 2017/0143262 A1 | 5/2017 | Kurunmäki et al. | |
| 2017/0173394 A1* | 6/2017 | Rider | A63B 24/0075 |
| 2018/0085630 A1* | 3/2018 | Capell | A63B 24/0075 |
| 2018/0140902 A1* | 5/2018 | Wiebe | A63B 24/0062 |
| 2018/0174685 A1 | 6/2018 | Hämäläinen et al. | |
| 2020/0001134 A1* | 1/2020 | Rauhala | A61B 5/6804 |

\* cited by examiner

METHOD, AN APPARATUS AND A SOFTWARE PRODUCT FOR PROVIDING A TRAINING PROGRAM

TECHNICAL FIELD

The application generally relates to providing an training program, and more particularly but not exclusively, the application relates to a method, an apparatus and a software product for providing a training program.

BACKGROUND

Fitness may be improved by planning of activities and a training program. Activities and a training program may be planned by a personal trainer and plans are based on a present condition or fitness level, as well as on a targeted fitness level or an aim of training. Currently, some automatic programs are available, which provide a training program based on predetermined training program templates.

SUMMARY

It is an aim to provide a flexible and adaptive training program. The training program provides training recommendations according to a set goal adaptively, taking into account detected workouts of a user.

According to an aspect of the invention a method for providing a next workout recommendation comprises:
  determining a present activity class of the user, which corresponds to a present fitness level of the user;
  receiving a training goal of the user, which relates to maintaining, increasing or increasing fast the fitness level of the user;
  determining a total target training load based on the present activity class and the training goal;
  detecting a sum of training load values for n-days from training history data, wherein n is an integer representing n-number of successive previous daily training session(s);
  detecting realized training load value(s) for performed daily training session(s) of at least one day from the training history data;
  determining a phase of a micro-cycle of successive training days for the next workout recommendation (NWR) by the realized training load value(s) for performed daily training sessions(s) of the at least one day, as a percentage of the sum of the training load values for n-days;
  determining a current training load target for the next workout recommendation (NWR) based on the present activity class, the determined phase of the micro-cycle and the sum of the training load values for n-days, and
  providing the next workout recommendation (NWR) for the following workout based on the current training load target determined for the NWR.

According to another aspect of the invention an apparatus for providing a next workout recommendation, the apparatus comprises:
  an arrangement configured to determine a present activity class of the user, which corresponds to a present fitness level of the user,
  an arrangement configured to receive a training goal of the user, which relates to maintaining, increasing or increasing fast the fitness level of the user;
  an arrangement configured to determine a total target training load based on the present activity class and the training goal;
  an arrangement configured to detect a sum of training load values for n-days from training history data, wherein n is an integer representing n-number of successive previous daily training session(s);
  an arrangement configured to detect realized training load value(s) for performed daily training session(s) of at least one day from the training history data;
  an arrangement configured to determine a phase of a micro-cycle of successive training days for the next workout recommendation (NWR) by the realized training load value(s) for performed daily training sessions(s) of the at least one day, as a percentage of the sum of the training load values for n-days;
  an arrangement configured to determine a current training load target for the next workout recommendation (NWR) based on the present activity class, the determined phase of the micro-cycle and the sum of the training load values for n-days, and
  an arrangement configured to provide the next workout recommendation (NWR) for the following workout based on the current training load target determined for the NWR.

According to yet another aspect of the invention a computer program product for providing a next workout recommendation comprises executable instructions, which when executed by a processor, are arranged to:
  determine a present activity class of the user, which corresponds to a present fitness level of the user;
  receive a training goal of the user, which relates to maintaining, increasing or increasing fast the fitness level of the user;
  determine a total target training load based on the present activity class and the training goal;
  detect a sum of training load values for n-days from training history data, wherein n is an integer representing n-number of successive previous daily training session(s);
  detect realized training load value(s) for performed daily training session(s) of at least one day from the training history data;
  determine a phase of a micro-cycle of successive training days for the next workout recommendation (NWR) by the realized training load value(s) for performed daily training sessions(s) of the at least one day, as a percentage of the sum of the training load values for n-days;
  determine a current training load target for the next workout recommendation (NWR) based on the present activity class, the determined phase of the micro-cycle and the sum of the training load values for n-days, and
  provide the next workout recommendation (NWR) for the following workout based on the current training load target determined for the NWR.

DESCRIPTION OF THE DRAWINGS

In the following embodiments are described in more detail with the accompanying drawings of which.

DETAILED DESCRIPTION

Figure 1:
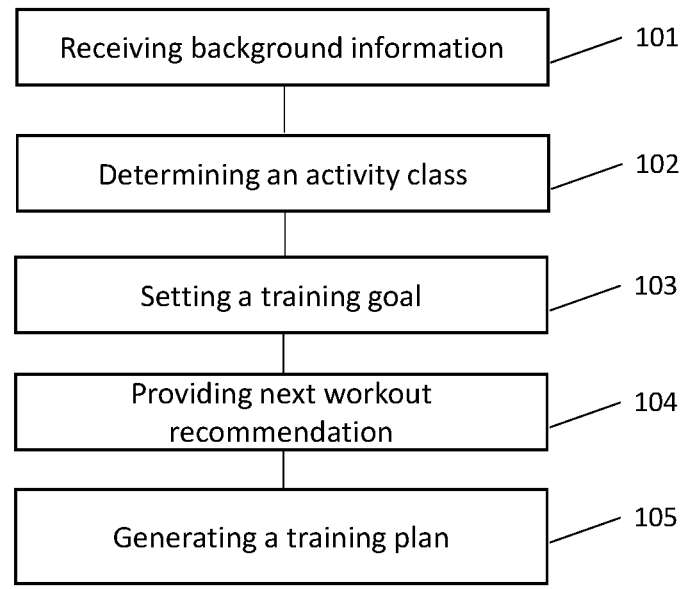
FIG. 1 is an exemplary flowchart illustrating a method for providing a next workout recommendation according to an embodiment.

The term fitness level refers to a property of a user. The fitness level of a user may be measured from a training history data including information on performed training(s) of the user. Alternatively or in addition, a user specific background information, for example from age, gender, height and/or weight, may have effect on the fitness level of the user. The fitness level of a user may be measured online during a training of the user. The fitness level may be measured via maximum aerobic capacity of a user, like a maximum oxygen consumption (VO2max) or a maximum metabolic equivalent (maxMET), for example.

A present activity class of a user may be determined using background information, such as age, gender, height and/or weight; a fitness level of the user; and/or training history data of the user.

The term training goal may be set or selected to be to maintain, increase or increase fast the fitness level of a user. A next workout recommendation (NWR) is determined for the user such that it supports the training goal. The term training plan refers to multiple following next workout recommendations.

A training load is a measure of how much the body's homeostasis has been disturbed with training, and it describes a physiological exercise load to a user by a given workout. A training load target is determined. The training load target level is dependent on a present activity class, which relates to a fitness level of a user. Absolute training load targets may be higher for higher activity class values than for lower activity class values. A weekly training load (WTL) may be determined based on the training load target. Although a target weekly training load (WTL) is referred to in this application, it may refer to a target training load for n-days, where n is integer, for example n=4-12, thus any number of days between 4-6 or 8-12 instead of seven days (a week). Correspondingly, a target monthly training load (MTL) may refer to a training target load for number of days, e.g. 24-38 days. Further, the weekly/monthly training load(s), or corresponding n-day training loads, may be used as a parameter(s) for determinations and calculations. WTL or a training load target of a block or of a month may be upgraded, being higher compared to user's prior training(s), in order to improve and increase the present fitness level or activity class of the user. For higher activity class values or fitness level of a user, the training load may not increase linearly, but less or modest, in order to avoid recommendation of too heavy exercise.

The terms training, exercise and workout may be used equally to describe a workout session or contents of it, which is performed or to be performed by a user. Training plan and training program refer to a training plan/program including two or more next workout recommendations.

Figures, e.g. FIGS. 1-3 and 6, illustrate flowcharts for implementation of embodiments, which are disclosed herein. It is noted that the order of phases illustrated in Figures is not required, but the various phases may be performed out of the illustrated order. In addition, certain phases may be skipped, different phases may be added or substituted, or selected phases or group of phases may be performed in a separate application, following the embodiments described herein.

FIG. 1 illustrates a method for providing a next workout recommendation. The method includes receiving background information in phase 101. Background information may comprise user specific information, like age, gender, height and/or weight. At least age is received as a background information. A maximum heart rate (maxHR) of a user may be estimated based on the age. The background information may be inputted by a user or available by accessing a memory of a user device or a remote server, or from alike source, wherein the background information has been saved.

The method comprises determining an activity class of a user in phase 102. The activity class refers to a general descriptor of a person's fitness level, activity history or training history. The present activity class may be evaluated using background information, such as age, gender, a fitness level (e.g. a maximum oxygen consumption value, VO2max) and/or training history data. A target exertion level for each planned exercise is determined individually for each person. The target exertion level of a user may be determined based on maximum heart rate (maxHR), of a user, which may be determined based on age, which is received as a background information in phase 101. Other background information in phase 101, or features derived from such, may also have an effect on the determination of an exertion level of a user. For example, fitness level may be estimated using background information optionally in combination with training history. Resulting fitness level may be used to determine target velocity, pace or power for different workouts. In a case where a user has performed exercise(s) by recording heart rate (HR) and positions, e.g. GPS positions; or HR and external power, it is possible to determine fitness level more accurately and thus the accuracy of target speeds and/or powers for workouts is determined more accurately correspondingly. Fitness level may be determined as described in U.S. Pat. Nos. 9,237,868 and 10,123,730. Further, other measured, calculated, detected or estimated values may have effect on the determination of an exertion level of a user. Measured values may comprise heart rate and heart rate variability (HRV) of the user. Thus, training history of a user, if available, may comprise information that has an effect on prescribed exertion level of a user. An activity class classification may comprise a scale, e.g. of 0-10, wherein 0 represents a sedentary person, while 10 represents highly fit/trained user, who exercises regularly. Each activity class has its own specific training load target. The training load target may comprise a range. The training load target comprises a lowest limit for a training load of the activity class. In addition, the training load target may comprise an upper limit for a training load of the activity class.

The method comprises setting a training goal in phase 103. The training goal may comprise to maintain or increase the present fitness level. Alternatively, the training goal may comprise to increase the present fitness level fast. The training goal may be time dependent. For example, time for achieving the set goal may be determined. If a user sets the time for achieving the training goal, the method may adjust the training goal, whether it is e.g. to increase or increase fast. The training goal may comprise short term and long term training goals. The training goal may comprise a target activity class, which is to be achieved.

The method comprises generating a next workout recommendation (NWR) in phase 104. The next workout recommendation is determined by the set training goal in phase 103 and the determined present activity class in phase 102. The NWR comprises a schedule and a training load target. A training load is a measure of how much the body's homeostasis has been disturbed with training, and it describes a physiological exercise load to a user by a given workout. For example, in case of a training goal being increase or increase fast, the training load is set slightly higher compared to the load requirements for maintaining the present determined activity class level of the user. The training load for the next training is set slightly higher in order to improve step by step over a number of next workouts, in accordance to the training goal, while maintaining a reasonable level of improvement. The method comprises providing a next workout recommendation to a user in phase 104. The next workout recommendation may comprise target training effect, HR zones and/or target duration of the next workout.

Figure 5:
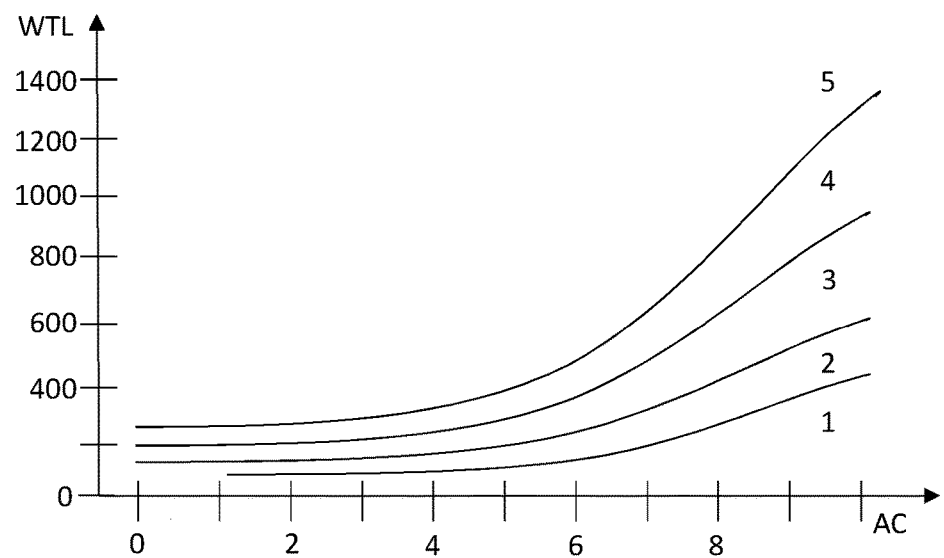
FIG. 5 is an exemplary illustrating graph for weekly training load coefficients according to an embodiment.

The next workout recommendation, as provided in phase 104, may be added as a history data in order to provide the following next workout recommendation. The following NWR thus takes into account the provided NWR. This may be repeated in order to provide a training plan in phase 105 comprising multiple succeeding NWRs. The training plan may comprise one/more block(s) of training. The total training load may be divided into blocks of training, which may include or form the schedule. A block may comprise a week, or other period of time, for example a period of 3-8 days. The block is one unit of successive days of workout recommendations. Blocks may be part of a bigger block structure, for example 3 successive 8-day blocks may be repeated. The training plan may be generated for the next workout recommendation only, or for example for one/more block(s) of training. The training plan may be defined taking into account amount of the total training load, which may relate to intensity, the determined present activity class and a training plan. In addition, a target activity class, number of rest days, and/or other parameters may have effect to the training plan. As an example, the training plan comprises a weekly training load target, which is based on the determined present activity class, which defines a lowest limit and possibly an upper limit of the weekly training load. A training load may be simplified using a relationship between the weekly training load and the determined present activity class in order to create a value for a training load coefficient. FIG. 5 illustrates relative training load coefficient values, which are represented on a scale from 1-5 based on the relationship between an absolute weekly training load and a determined present activity class.

Figure 2:
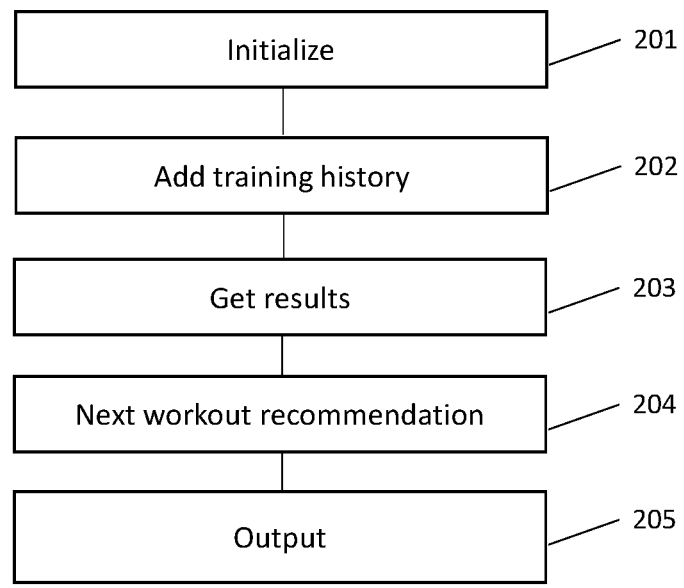
FIG. 2 is an exemplary flowchart illustrating a method for generating a next workout recommendation according to an embodiment.

FIG. 2 illustrates a method for generating a next workout recommendation based on previous workout data according to an embodiment. Method of FIG. 2 comprises an initialize phase 201. The initialize phase 201 may be started in response to a user request for providing a next workout recommendation. At the initialization phase, background parameters may be fetched and/or inputted. Background parameters may include gender, age, height and weight of a user. In addition, background parameters include the current date information. A next workout recommendation (NWR) is provided for the current date, i.e. today at the time of initializing, or alternatively for the following day. If it is recognized that the user has already performed a predetermined amount of training at the current day, the NWR is provided for the following day. Background parameters relating to the present fitness level of the user, like maximum metabolic equivalent (maxMET) and/or maximum oxygen consumption (VO2max); and maximum heart rate (maxHR) may be fetched, inputted or evaluated based on the other provided background parameters. For example, maxHR of a user may be determined based on age of the user, and VO2max and/or maxMET may be determined from user's training history data, which includes information on previous workouts/trainings as performed by the user.

The method illustrated in the FIG. 2 comprises an add training history phase 202. The add training history phase 202 may comprise adding a training history information of a user from a predetermined number of previous days. The training history may be fetched from a local or remote memory or data source. The training history comprises data on previous exercises in a chronological order, as performed by the user. The training history may comprise exercises from the past days, for example from past 14, 28, 37 or 42 days. The training history may comprise date and time information, a training load peak information, resource recovery time and fitness level for each performed training, as well as a type of the training. The date and time information may comprise time of ending the training. The training load peak information, the resource recovery time and the fitness level may be calculated in real time by a real time calculation engine that comprises as an input an interbeat interval and/or a heart rate level data, and optionally an external workload, like speed and altitude or external power output. Type of exercise may comprise identifying the type of training, for example running, cycling or other.

A present activity class (AC) of the user is determined. In case no information on previous training history is available, the present AC may be determined based on user's present fitness level, e.g. via maximum aerobic capacity of a user, which may be calculated in phase 202. In addition or alternatively, variables of training history data may be estimated and/or calculated based on initialization data and/or background parameters of phase 201. The following get results phase 203 is optional, and it may be skipped, if no training history information is available.

If the training history is available in phase 202, the next phase may be get results in phase 203. The get results in phase 203 may provide information about the performed training(s) and development status of the user. The user gets information about personal fitness level development and intensity of the past training(s), for example being at a correct level, too hard or too low. In a get results phase 203 present/previous training load of the user is estimated. The scale of the present training load may be low, medium or hard, for example. Get results phase 203 may output values and trends based on past training history of the user, as performed. Get results output may comprise information relating to a daily training loads, to a weekly training loads and/or to a monthly training load. Get results may comprise information relating to training load, like a trend for a training load, a sum of the weekly training load, an optimal minimum and maximum for the weekly training loads, and a difference of the exercised weekly training load sum, if below the optimal minimum or above the optimal maximum. Get results may comprise information relating to fitness percentile, fitness class, fitness level and changes of such. Get results phase 203 is optional and used for providing information to a user.

Based on information provided in phases 201-202, with or without the optional phase 203, an activity class of a user is determined. The activity class of a user may be updated based on the provided information. In addition, a training goal may be inputted by a user, fetched from a data storage or determined based on inputted target time or other parameters, for example. The training goal may be to maintain, increase/boost, or increase/boost fast.

Based on available information, a next workout recommendation (NWR) is provided in phase 204. The next workout recommendation comprises a recommendation for a workout that the user is recommended to perform next. The recommendation included in the NWR may be to rest. The next workout recommendation may comprise information on recommended workout, like a target training effect, a duration, a phase of a training cycle, a distance, intensity limits, hear rate limits and/or speed limits. The next workout recommendation information is outputted in phase 205 with at least some variables relating to the NWR. For example, the type being running and a running distance may be outputted.

In order to provide the NWR, the actual realized training load values may be detected, as performed by the user. The performed training load values may be detected for at least one or two past training sessions)/day(s) from training history data, With aid of the past performed training load value(s), a target intensity for the NWR may be evaluated.

The next workout recommendation may be determined for more than one following trainings, as a training plan. A user may request a training plan including NWRs for a number of following days. Typically trainings are recommended one per day. For more than one following trainings, a training plan is made for the same number of days. For example, five following exercises are provided for the following five days. The following 5 days may include the current date, if the user has not yet performed a training at the current date. In case a number of following NWRs are requested, a single next workout recommendation NWR, for today or for tomorrow, is provided first. The single provided next workout recommendation and its details are added to the data, that is used for providing a successive NWR. Again, the latest provided NWR is added to the data that is used for providing the successive NWR(s). Thus, each provided NWR has an effect on the following NWR(s) for the following days. It is assumed that the provided NWRs are followed and the user is performing exercises in accordance to provided NWR(s). Providing more than one next workout recommendations for the more than one following days is presented in more detail with FIG. 3.

Method phases and blocks of Figures may represent program logic, which is executable by a processor and stored in a memory of a computer program product or an apparatus. A user may input number of days, for which they wish to receive workout recommendation(s), and a training goal, which may be to maintain, increase or increase fast. Number of days and a training goal may be called input variables. With the inputted variables and/or information, phases as illustrated in the FIG. 2 may be executed in order to provide an output for a user. The output may comprise output variables. The output variables may comprise a training effect, a duration, a phase, a distance, intensity limits, heart rate limits, speed limits, and power limits. A training effect relates to a target training effect of the NWR(s). The training effect may be scaled as a range, for example in numbers, representing training effects from a none or light exercise to an extreme exercise. A duration describes duration of the recommended workout, for example in minutes. A phase relates to a phase of training, which may include easy, medium/moderate or hard phases. Different phases are repeated in accordance to a predetermined cycle. A training plan may be divided into blocks. The training plan may provide phases that change after each block, like a 7-day block or an 8-day block, which are repeated in the order of: easy, medium/moderate, hard, easy, and so on. The cycle of blocks may be called a meso-cycle and it is illustrated with FIG. 4. A present phase of the meso-cycle, i.e. cycle of the blocks, may be determined and the detected phase of the meso-cycle has an effect on target training load(s) for the NWR(s). It is possible to automatically detect a preferred phase for the next workout recommendation, even when a user has not been following the training plan(s) or the previous NWR(s). Variating loads between the meso-cycles of blocks enables speeding up fitness development of the user. A distance relates to recommended length of the next workout, for example in kilometres or meters. Intensity limits for the next workout may be presented as a range between intensity limits. Intensity limits may be calculated as a percentage of determined maximum oxygen consumption, VO2max. Heart rate limits for the next workout may be presented similarly as the intensity limits by providing a minimum and a maximum limit values. Heart rate limits may be presented in beats per minute. Heart rate limits may be calculated as a percentage of a maximum heart rate, maxHR. Similarly, a minimum and a maximum limit for speed during the next workout may be determined. The speed may relate to running speed, or power limits for cycling or indoor rowing, for example. Training load of past workouts enables providing information on the training rhythm, or a phase of cycle of workouts. The cycle of workouts/trainings may be called a micro-cycle. The training sessions proceed in a predetermined order of alternating easier and harder training days while having rest days in between the two. A four-day micro-cycle comprises training sessions of easy-rest-hard-rest. Detecting the phase of the micro-cycle of workouts enables outputting such workout loads for the current, upcoming next workout recommendation(s) that are physiologically sensible. This includes alternating between easier and harder training sessions, while including rest days. A training session corresponds to a single day such that a training load of performed training session(s) is calculated as a sum of the daily trainings in case more than one training sessions are performed during a single day.

Figure 3:
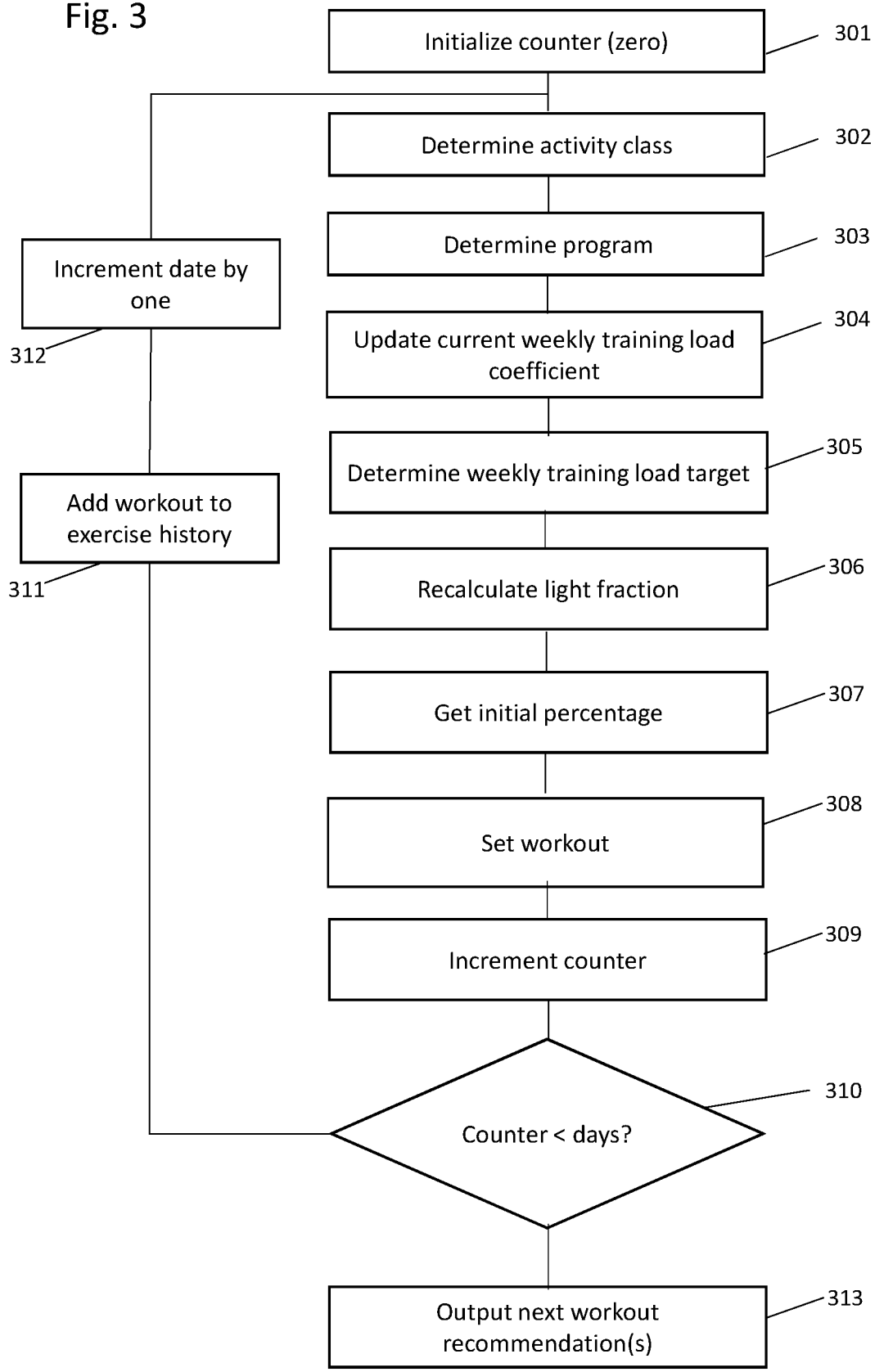
FIG. 3 is an exemplary flowchart illustrating a method for generating a next workout recommendation according to an embodiment.

FIG. 3 illustrates a method for providing one or more next workout recommendation(s). The NWR(s) may be provided for one or more following workouts, which are provided one per day. A user may request a training plan comprising workout recommendations for number of days. The number of days may be determined as 7 days, for example, or it may be inputted by a user. A counter is initialized to a value zero in phase 301. The counter is used for counting number of NWRs provided. For each requested NWR or day, one iteration of the loop, as illustrated in FIG. 3, is executed. For example, following seven NWRs for the next following seven days are provided by executing seven iterations of FIG. 3.

A present activity class is determined in phase 302. The present activity class, AC, is determined for the present day at the time. The present AC determination may employ determining a present monthly training load (MTL), and a present fitness level. The activity classes have predetermined training load limits. Different fitness levels, which may be presented via latest maxMET and/or VO2max, represent different activity classes. Larger of the activity class (AC) levels, as determined via the present monthly training load (MTL) and the present fitness level, may be selected as the present activity class (AC). If a training goal is to maintain the present activity class, the present activity class (AC) may be determined based on the latest fitness level, e.g. via maxMET. If a present monthly load and the latest fitness level cannot be determined, a default value may be used as a present activity class AC. An activity class may comprise predetermined scaled values, e.g. in range of 0-10.0.

A training goal is determined in phase 303. The present training goal may be to maintain, increase or increase fast the fitness level of the user. The training goal relates to a goal or a target for the training. The training goal may be inputted by a user or adjusted. The adjustment may be done based on the determined present activity class (AC) of the user, or based on inputted time for achieving the training goal. The user may wish to maintain the present activity class or increase it either at a faster or a lower pace. In case the present activity class (AC) of the user is at above a predetermined high level, like value 8 of AC values between 4 to 10, the training goal may be adjusted to be maintain. This may be done to avoid providing uncomfortably hard training program for a user.

A present weekly training load (WTL) coefficient is updated in phase 304. The WTL coefficient is a relative value based on an absolute value of the present WTL. The present WTL is based on detected training load peak values from performed trainings during the week. The present WTL describes amount of training the user has performed during the past week including today. The weekly training load coefficient may be determined based on the present training goal, as determined in phase 303, and the present activity class (AC) as determined in phase 302. The present weekly training load (WTL) coefficient may be represented as a value in a predetermined range, for example in a range of 1.0-5.0. The "week" or "weekly" may be replaced by n-number of days, wherein n is integer, e.g. n=4-12.

A training plan is divided into cycles of blocks of training intensities, called meso-cycles (of blocks). A meso-cycle may comprise one/more four-day micro-cycle(s) of training days comprising medium and high intensity training days having a low intensity training day after each medium and high intensity training day. A present phase of the micro- and/or meso-cycle may be detected. Detecting the present phase of meso-cycle enables determination of the current following NWR being at a block of low, moderate/medium or high intensity training. By determining two previous performed phases of the micro-cycle, the present phase of the micro-cycle, relating to the training to be recommended, may be determined based on predetermined successive four-day micro-cycles. In alternative to a short meso-cycle comprising a four-day micro-cycle, the training intensities may also follow a longer, more slowly proceeding meso-cycle(s) comprising more than one micro-cycles. For example, the training intensities may be varied over 24 days formed of three meso-cycles of blocks. Two successive 4-day micro-cycles (days 1-8) form an easy block, which are first (to be) carried out at an easy level. The following two successive 4-day micro-cycles (days 9-16) form a moderate block, which are then (to be) carried out at a moderate level. Finally, the following two successive 4-day micro-cycles (days 17-24) form a hard block, which are then (to be) carried out at a hard level. The easy block, the moderate block and the hard block form a meso-cycle of blocks, which may be repeated. This is described in more detail with FIG. 4.

The micro-meso-cycle phase detection may include detecting training load peak values from a training history data. Detecting a phase of a micro-cycle includes presenting the training load peak values as a percentage of WTL target. Thus, the training load peak values are normalized with respect to WTL target. Utilizing normalized values enables the same micro-cycle phase detection method to be used for all activity classes and for all training plans. A phase detection of the micro-cycle may be simplified and straightforward.

A phase detection of a meso-cycle may use training load peak values. The meso-cycle phase detection may utilize raw values instead of percentage values, as in case of micro-cycle phase detection. A meso-cycle phase detection comprises detecting locations of micro-cycles (of improve-rest-maintain-rest). Location of previous complete block is inferred from the micro-cycles. For example, according to the previous example, location of previous complete 8-day block, including two micro-cycles, is inferred. Sum of training load peak values over the block (e.g. 4 days, or as in the previous example, 8 days) is calculated. The sum is scaled in order to be comparable with WTL (or training load of n-day, if applicable) target values. For the 8-day block and in case of WTL target values, the sum is scaled by 7/8. The WTL (or n-day training load) target values are associated with easy, medium or hard blocks at the current AC. If the previous block was detected as easy (/medium/hard) the current block is determined as medium (/hard/easy).

A phase of a meso-cycle of 24 days, and three 8-days blocks, wherein each block consists of two 4-day micro-cycles, may be automatically detected based on the training load peak values in the 38-day training history. The method may be automated as follows:

In the training history of 38 days, find the index of the first training day (i.e., the first day with non-zero training load peak value). This index, i_start, gets an integer value between 1-38, where the index 38 corresponds to the current day, index 37 corresponds to yesterday, etc. The If the training history is empty
set the value of i_start to 38.

If there is a long (say, longer than 5 days) break in training in the middle of the exercise history
set i_start to the index of the first training day after this break.

If this long break occurs at the end of the training history (i.e., there are no training days after the break), set the value of i_start to 38.

If the difference between the index of today (e.g., i_today=length of training history list, 38 in this example) and i_start is less than, say, 30 (i.e., i_today−i_start<30), the current index in the mesocycle i_meso=1, 2, . . . , 24) may be determined simply based on this difference:

i_meso=modulo(i_today−i_start, 24)+1 (now, i_meso gets a value in the range 1-24)

Now, if i_meso is between 1-8 (9-16/17-24), the current ongoing block is of easy (moderate/hard) intensity. Set the intensity of the current ongoing block to this value (easy/moderate/hard), and exit the procedure.

Otherwise, the intensity of the current ongoing 8-day block is determined using the realized training load peak values in the 38-day training history:

High-pass filter the 38-day sequence using a FIR-filter which emphasizes the starting locations of the 4-day micro-cycles. In its simplest form, the FIR filter may be of length 4 and its coefficients may get the values

[7.0, −4.5, 2.0, −4.5]. The FIR filter should give large positive values for those days which are clear starting points of a 4-day micro-cycle. Set the last four elements of the filtered sequence (corresponding to indices 35-38) to zero (since we are interested only on micro-cycles that have been fully completed)

Find the location of the largest element in the filtered sequence (i_max) as well as the location of the largest element within in the index range 31-34 (i_max_near).
  if i_max is in the range 35-38 (i.e., if positive values were not found), set the intensity of the current block to easy and exit the procedure.

If i_max is smaller than 31 (i.e., if the location of the starting point of the strongest micro-cycle has occurred more than 8 days before today) and if the filtered value at the index i_max_near is larger than the filtered value at the index i_max multiplied by the constant 0.5 (i.e., tlp_f[i_max_near]>0.5*tlp_f[i_max])
  we conclude that the day at the index i_max_near is most likely the starting location of the nearest fully completed micro-cycle. Thus, we set i_nearest_micro_cycle=i_max_near.

Otherwise
  we increase the value of i_max by increments of four until i_max is greater than 30.
  Then, we check whether the training load peak values at the index locations (i_max−1) and (i_max+1) are both smaller than the training load peak value at location i_max. If this condition does not hold, we decrease the value of i_max in steps of one until either the value of i_max becomes one or the aforementioned condition holds.
  If we the value of i_max is still greater than 30, we set i_nearest_micro_cycle=i_max. Otherwise, we conclude that a clear starting day of a fully completed micro-cycle was not found in the near past (within the past 8 days), we set the intensity of the current block to easy and exit the procedure.

Now, the index i_nearest_micro_cycle corresponds to the day of the previous fully completed micro-cycle and its value is in the range 31-34. Now, there are two possibilities: the micro-cycle starting on day i_nearest_micro_cycle is either 1) the first day of the current ongoing 8-day block, or 2) the fifth day of the previous 8-day block. Which one of the two possibilities is correct may be determined via comparing the training load peak sums of the three consecutive 4-day blocks (micro-cycles):
  sum_a: sum over days i_nearest_micro_cycle−8, i_nearest_micro_cycle−7, i_nearest_micro_cycle−6, i_nearest_micro_cycle−5
  sum_b: sum over days i_nearest_micro_cycle−4, i_nearest_micro_cycle−3, i_nearest_micro-cycle−2, i_nearest_micro_cycle−−1
  sum_c: sum over days i_nearest_micro_cycle, i_nearest_micro_cycle+1, i_nearest_micro_cycle+1, i_nearest_micro_cycle+3

If the absolute difference between the sum_a and sum_b is smaller than the absolute difference between the sums sum_b and sum_c, the case 2) above holds and we set i_nearest_full_block=i_nearest_micro_cycle−8.
  Otherwise the case 1) above holds and we set i_nearest_full_block=i_nearest_micro_cycle−4, Now, i_nearest_full_block is the index of the starting day of the previous fully completed 8-day block and its value is in the range 27-30. We next determine the effective realized weekly training load over this 8-day block via summing all training load peak values over these eight days and scaling the result with the constant 7/8. Then, we compare the obtained value, wtl_sum_nearest_full_block, with the weekly training load target values of the three possible block intensities using the current activity class and the WTL coefficient values used in the current training program:
  wtl_target_easy: weekly training load target corresponding to the easy 8-day block
  wtl_target_moderate: weekly training load target corresponding to the moderate 8-day block
  wtl_target_hard: weekly training load target corresponding to the hard 8-day block If wtl_sum_nearest_full_block is closest to wtl_target_easy (wtl_target_moderate/wtl_target_hard), the previous fully completed 8-day block was easy (moderate/hard), and the current block must thus be moderate (hard/easy). Set this value to the current block intensity and exit the procedure.

The phases of micro-cycle and/or meso-cycle may be detected automatically either from the latest performed and fully completed daily training, as recommended in NWR, and/or adaptively from the realized training load peak values in the training history data. The latest fully completed daily training, corresponding to the training as recommended in NWR for the day, may be performed on the previous day or on the present day (today). The current phase of the micro- and/or meso-cycle (for NWR) is determined to be the following phase of the micro- and/or meso-cycle, and it is based on the previous detected phase(s) of the corresponding cycle(s). If the detected current phase of the meso-cycle of blocks (for the following NWR) is determined to be "easy", the value of the target weekly training load coefficient is adjusted downwards. If the detected current phase of the meso-cycle is "hard", the value of the target weekly training coefficient is adjusted upwards. During detected moderate blocks of the meso-cycle, the target training load coefficient may not be adjusted. An adjustment may be done by adding or subtracting the target weekly training coefficient by a positive offset value, which is added to (/subtracted from) the present weekly training load coefficient value in the case of an hard (/easy) phase of a meso-cycle. The offset value is a predetermined value, which may be determined based on the present training goal and the present activity class.

Weekly training load, WTL, target is determined 305. The WTL target takes into account AC and WTL coefficient. Based on the determined present activity class in phase 302, a value for a weekly training load target limit may be linearly interpolated from the predetermined offset values. For example, the weekly training load coefficient value of 3.5 corresponds to the midpoint between the two centremost lines (at a given activity class) in FIG. 5. Alternatively or in addition, weekly training load target limit values may be tabulated in a table and associated with each activity class. The WTL target may be replaced by n-days training load target. The WTL target may be used as a normalizing constant, which makes it possible to use percentage values and limits for all activity classes and for all training plans.

A light fraction is recalculated in phase 306. The light fraction refers to a ratio between the lowest training load peak value of the week, which gives rise to a training effect (TE) of 1.0, and the present weekly training load sum. The present weekly training load sum, which refers to the realized WTL sum, is determined by the sum of the detected training load peak values from the present day and past 6 days. Correspondingly, detected peak values from today and (n−1) previous days may be used instead of "week". The WTL may be represented as WTL coefficient.

An initial percentage is provided in phase 307. The initial percentage for NWR may be called an NWR candidate. The initial percentage relates to a ratio between the training load peak value of the current NWR and the present weekly training load target. A ratio between a training load peak value of the current prepared NWR and the present weekly training load target is chosen by using similar ratios for today, yesterday and the day before as inputs. The initial percentage or the NWR candidate may be estimated based on a decision tree. The decision tree proceeds step by step taking into account realized training load values of two previous trainings, as a percentage of the WTL target. The realized training load value for a given day is defined as the sum of the training load peak values of all exercises carried out during that day. Representing the realized training load value of a day, as a percentage of the WTL target, enables using same percentage limits in case of all activity classes and all training plans. This simplifies determination of a phase of a micro-cycle. In case the training load percentage of the previous training day falls below a predetermined percentage, the corresponding percentage value of the day before the previous training day is taken into consideration. The percentages are compared to a predetermined percentage ranges. In addition, the present weekly training load, WTL, and determined recovery time may be taken into account. If the present recovery time is very high, for example greater than or equal to several days, e.g. 28-58 hours or more, the initial percentage of NWR, as determined in phase 307, is lowered or downgraded to rest or light training from maintain; or to maintain from increase. The downgraded initial percentage of NWR or, in case of no downgrading, the initial percentage of NWR is set as the final percentage value for NWR. The decision tree includes predetermined rules for determining the initial candidate for the training load peak (relative to the present weekly training load sum) of the next recommended workout. A decision tree is described in more detail with FIG. 6.

A workout is set in phase 308. A training load peak target value for the next workout may be obtained by multiplying the present weekly training load target value by the final percentage value. The training load peak target value may be transformed into a training effect value based on the present activity class (AC). Duration for the current exercise is selected based on the present activity class and the final percentage value in view of the predetermined offset values. Finally, intensity of the exercise, heart rate limits, speed of the exercise and distance may be determined. The determinations of intensity, heart rate limits, speed and distance may be carried out via a simulation at a constant intensity. The used constant intensity may be determined using binary search and intensity limits may be determined to be at a certain percentage, for example 4-12%, below and above the determined target internal intensity value. The heart rate range and speed of exercise may be determined via linear transformation from the intensity range. The distance may be linearly estimated from the duration and mean speed. A target intensity may be calculated by using training load target and set time, i.e. duration target, for example as presented in publications U.S. Pat. Nos. 7,805,186, 8,052,580, 8,465,397. If training load target and duration target are determined or known, then the target of internal intensity (e.g. as % HRmax or % VO2max) may be determined by simulating different intensities. Alternatively, if target of internal intensity is known, then external workload target, which may be e.g. target speed or target power, may be determined based on a fitness level of a user. A target speed and distance for any workout may be calculated by utilizing a fitness level of a user, as presented in publications U.S. Pat. Nos. 7,805,186, 8,052,580, 8,465,397. A fitness level of a user may be determined as described in this application, and/or in combination with methods as presented in publications U.S. Pat. No. 9,237,868, U.S.101233730.

A counter is incremented, in phase 309, by value of one corresponding to one implemented loop including phases 302-308. The counter value is compared with total number of trainings/days in phase 310, where the total number of the trainings/days corresponds to trainings/days of the training plan, as determined or requested by the user. If the counter value is less than the total number of trainings in phase 310, the contents of the prepared NWR are added as part of the workout history data in phase 311 and the date is incremented by one in phase 312. Next loop for determining the following next workout recommendation, NWR, continues from phase 302. This enables each prepared next workout recommendation to have effect on the following NWR(s) of the following day(s). After the next workout recommendations are prepared according to phases 302-308 for the predetermined or the requested number of days, the next workout recommendation(s) are outputted in phase 313. The determined next workout recommendation(s) are presented to the user.

Figure 4:
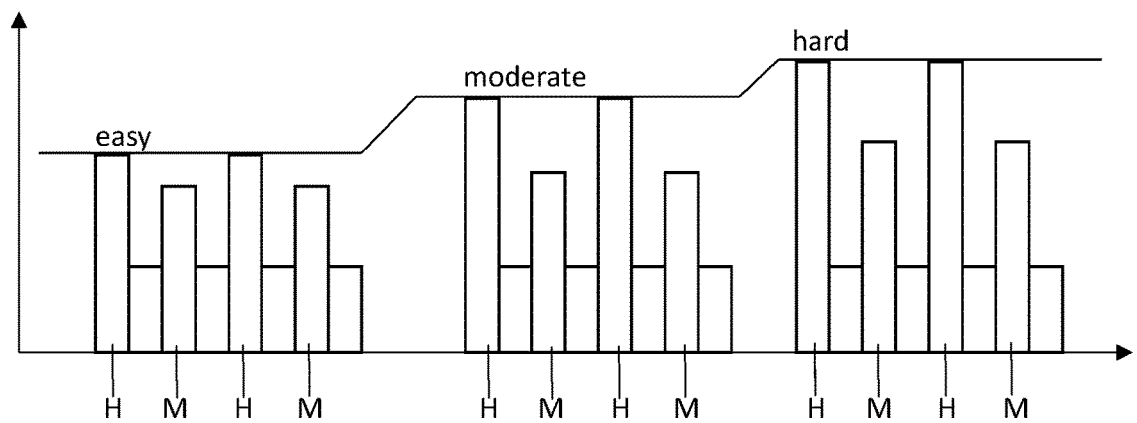
FIG. 4 is an exemplary graph-diagram illustrating training blocks and cycles according to an embodiment.

FIG. 4 illustrates training blocks and cycles according to an embodiment. A training plan comprises a total training load, which may be divided into training blocks. A training block may comprise n-number of days, for example. Each bar of FIG. 4 represent a day. Blocks of FIG. 4 are 8-day blocks. Time is illustrated in x-axis of FIG. 4. FIG. 4 illustrates a meso-cycle of three 8-day blocks, where the blocks illustrate easy, moderate and hard intensity trainings. Each training block comprises target load levels for a training load. A target training load for a training block is set based on the training goal. Intensity is illustrated in y-axis, and it may be illustrated as training load values, e.g. of 0-120; or as training load coefficient values, e.g. of 0-5. Each block comprises 8 training days, or two micro-cycles of four days, wherein training is divided to days of high intensity training H for improving training sessions, days of medium intensity training M for maintaining training sessions, and rest days after each day of a high intensity H or a medium intensity M. The micro-cycle of training sessions of improve-rest-maintain-rest is repeated. As illustrated in FIG. 4, days of improving training sessions H and maintaining training sessions M have a higher level at a hard intensity training block compared to moderate intensity training block, which has a higher level for days of improving training sessions H and maintaining training sessions M compared to those of an easy intensity training block. This enables providing variation to training plans by providing different training blocks of easy, moderate and hard. A moderate intensity training block may be determined to correspond to weekly training load target level. An easy intensity training block may be determined to correspond to weekly training load target level diminished by an offset value. A hard intensity training block may be determined to correspond to weekly training load target level added with an offset value. The offset values are predetermined and dependent on the present activity class of the user, and based on physiologically reasonable progression for the training load. Training durations may differ among different training days and/or training blocks. In addition, the training plan is adapted in accordance to trainings performed by a user, which may be monitored. A training plan may be updated in accordance to monitored trainings performed by a user. If user takes a rest day or performs less than planned; or alternatively exercises with higher intensity than planned, the next workout recommendation takes the user performed workout(s) into account. The training plan is adapted based on monitored user performance. The adapting is based on a training goal, which may be to maintain, increase or increase fast the fitness level of a user. The provided next workout recommendation is recalculated based on the true realized training history each time the procedures described in FIGS. 2 and 3 are repeated. If the user does not follow the provided training plan (or NWR), the training plan including NWR(s) generated for the successive day(s) is adjusted accordingly. In addition, for example a present activity class of a user is updated, since it may change during a training plan.

The training goal may include long term and short term goals in order to increase or maintain a present fitness level. The training goal may optionally include increasing or maintaining the present fitness level within a specified length of time. For example, a weekly training load WTL target is defined as 7 days training load sum, based on any type of cumulative training load measure, which may include a training impulse score (TRIMP). If a training goal is to increase, the training goal may be used to automatically set WTL target(s) to an upgraded (higher) level than for a training goal of maintain. If WTL targets for each training week are at an upgraded, higher level, then also monthly training load (MTL) is at an upgraded level. An upgraded level of a training load target enables developing user's fitness level, and correspondingly the present activity class, whereas training load target with no upgrading enables maintaining the present activity class.

A target load level is determined separately for each activity class, for each phase of the meso-cycle of the training block (easy/moderate/hard) and for each training target (increase/increase fast/maintain). Thus the target load level is dependent on a current determined activity class, which relates to a fitness level of a user. Absolute training load targets are higher for higher activity classes than for lower activity classes. In case the user has a low fitness level, a weekly/monthly target load WTL/MTL, or a training target of a block, may be upgraded, being higher compared to user's prior training(s), in order to improve and increase the present fitness level or detected activity class of the user. For higher activity classes, the training load may not increase linearly, but may be less or modest, in order to avoid recommendations of too heavy exercise. In addition, an offset value, which may be used for adjusting values or variables, is determined for each activity class. The training blocks may comprise micro-cycles of maintain-improve-recovery training sessions. Maintain, improve and recovery training sessions comprise different training loads correspondingly. Maintain, improve and recovery training sessions may be utilized in order to improve the present fitness level of a user effectively, as planned, and/or in order to provide variation to the training plan and/or among training blocks. The target training load (TL) of a block, or the corresponding TL coefficient, for a moderate block may be set as a reference training load. The target training load for an easy block may be set as the reference training load subtracted by the offset value. The target training load level for a hard block may be set as the reference training load added by the offset value. This is illustrated in tables 1-3 later in the description.

In order to make or update a training plan, effects of previous performed workout(s) on a user (body homeostasis) are determined. Excess post-exercise oxygen consumption (EPOC), a training impulse (TRIMP) or some other parameter may be used as a cumulative measure for a training load. EPOC is a physiological measure that reflects the recovery demand and the disturbance of the body's homeostasis brought on by the exercise. EPOC may be derived from monitored athletic training and physical activity. EPOC may be calculated, estimated or predicted based on heart rate, heart rate variability or other workout intensity derivable parameter. Other data, in addition to monitored workout data, may be taken into account in order to determine a training load. For example, information related to a recovery state of a user may be utilized. A recovery state may be monitored based on heart rate variability (HRV) or parameters derived thereof, for example. Calculation of EPOC, TRIMP, training effect (TE), and cumulative training load may utilize information on exercise intensity during workouts. Intensity may be derived from user heart beat information by using one/more heart beat derivable parameters, which may include heart rate variability (HRV), heart beat frequency (bpm, beats per minute), respiration rate (breaths per minute), a measure describing increase/decrease/unchanging exercise intensity, or other alike parameter(s). Intensity of an exercise may be determined based on a distance travelled, a duration of an exercise and user's physiological characters, like fitness level, which may be measured as VO2max.

A training plan may be based on a detected training load, recovery time, order of performed workouts, training history data or analysis of such, training load distribution, present training status and/or detected phase of the meso-cycle and/or the micro-cycle of training intensities of previous (performed) workouts.

Figure 6:
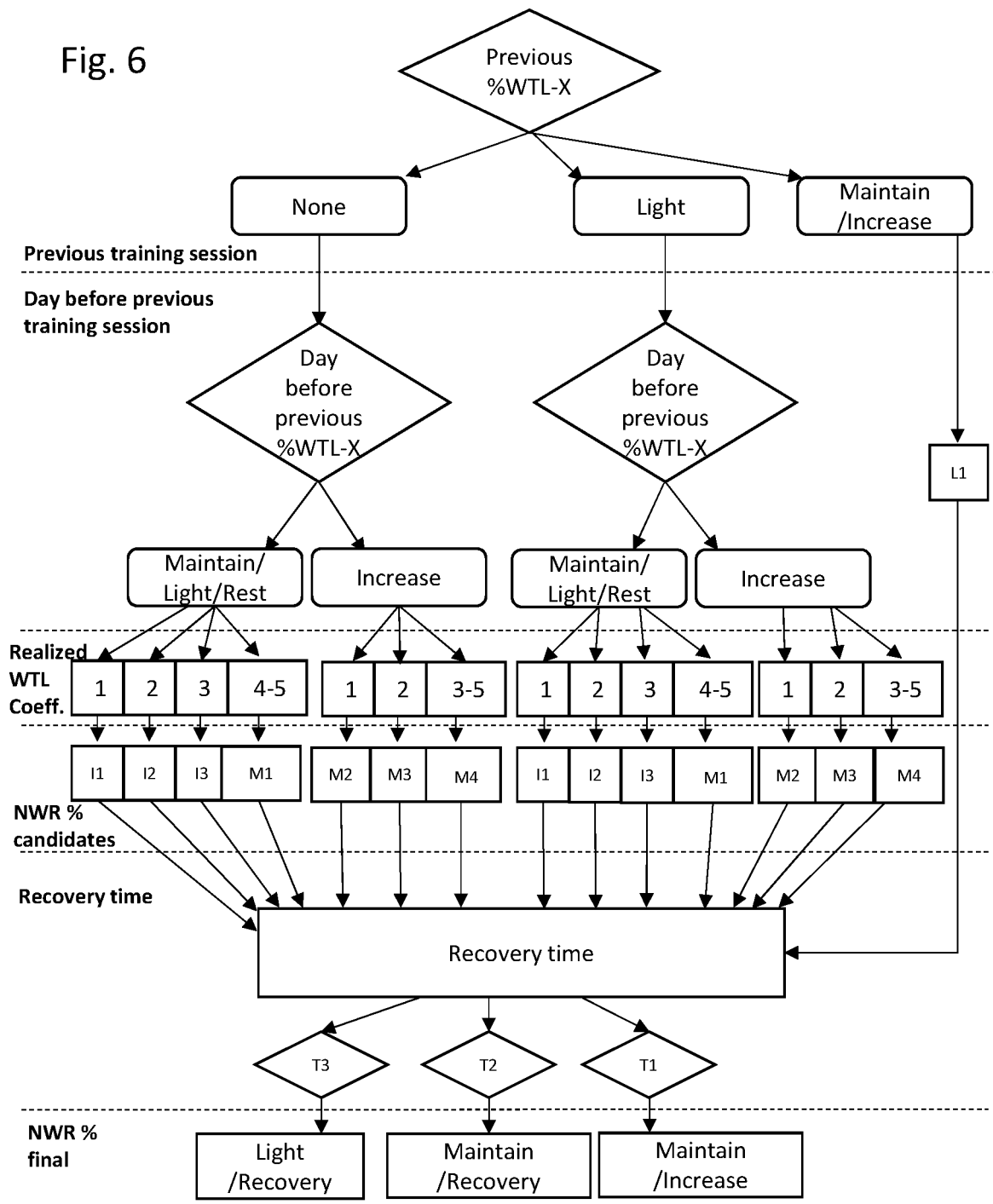
FIG. 6 is an exemplary flowchart illustrating a decision tree according to an embodiment.

The method of FIG. 1, optionally in combination with FIG. 6, enables generating the next workout recommendation without training history data. In this case, some assumptions may be made, like a lack of activity during the past one or two days. In addition, a default training goal may be used instead of setting or determining one based on a user input. The user is being monitored, e.g. via a wearable monitor device. During a workout a user's fitness level is estimated, e.g. via VO2max or maxMET, and it has effect on determination of the present activity class of the user. Each activity class has a predetermined lower limit values for fitness level parameters (e.g. VO2max, maxMET), representing the present fitness level of a user. The larger of the activity class levels, as determined via the present monthly load and the present fitness level, may be selected as the present activity class (AC). The predetermined limits may be determined separately for different age groups and for male and female users. For example, a determined fitness level value for an older person (e.g. age of 60 years), leads to determined AC being higher compared to the same determined fitness level value for a younger person (e.g. age of 40 years). After the first or the next monitored workout of a user, the present activity class of the user may be updated based on the previously estimated VO2max, or other parameter. Detected load of a workout performed by a user has an effect on the training load of the next workout recommendation. After it is detected that the user has performed one or more workouts, next workout recommendation (NWR) is generated based on the detected data from the workouts. The next workout recommendation may be updated based on the detected data.

FIG. 5 illustrates a graph for weekly training load coefficients. Activity class (AC) values are presented in x-axis. In FIG. 5 AC values in x-axis are presented in the scale of 0-10. Weekly training load (WTL) values, which may be called absolute WTL values, are presented in the y-axis. In FIG. 5 WTL values in y-axis are presented in the scale of 0-1400. Curves of FIG. 5 present WTL coefficient values, which may be called relative WTL values, based on the present activity class (AC) and the present weekly training load (WTL). Each activity class (AC) value has their own, specific training load coefficient limit values.

A training load describes a physiological exercise load for a given workout, training or exercise. A training load is compared to a target range, which is based on a set goal, representing a desired fitness level or a target AC of a user. The weekly training load (WTL) coefficient values are visualized in FIG. 5. A weekly training load (WTL) coefficient may be represented, for example, a relative value in the range of 1.0-5.0, where the values 1.0-2.0 correspond to the absolute weekly training load values between the zero and the lowest curve (horizontal, x-axis), the value 2.0-3.0 corresponds to the absolute weekly training load values between the two lowest curves. This represents an easy WTL target for the given activity class. A WTL coefficient value between 3.0-4.0, being the range between the two centre-most lines of the FIG. 5, represents a medium weekly training load peak sum for the given activity class. Likewise, the weekly training load (WTL) coefficient may get a value in the range of 4.0-5.0, when the absolute WTL value is between the two uppermost lines of FIG. 5, and this represents a high weekly training load (WTL) target for the given activity class. When the current activity class (AC) and the absolute weekly training load (WTL) sum are known, the present WTL coefficient value(s) may be determined from FIG. 5, as the corresponding slot between the curves of FIG. 5. The curves illustrate the locations of the integer values of the weekly training load (WTL) coefficient between 2-5 for each activity class (AC). For example, the integer part of the WTL coefficient is two in the region between the two lowest curves. There are other ways to present training effect based on AC and WTL. For example, for each AC, upper or lower limits of WTL target, which corresponds to a certain training load (WTL) coefficient, may be tabulated. An example tables comprising target weekly training load coefficients are presented in the following tables 1-3, where table 1 presents target weekly training load coefficients for training goal of maintaining, table 2 presents target weekly training load coefficients for training goal of increasing, and table 3 presents target weekly training load coefficients for training goal of increasing fast.

TABLE 1 weekly training load coefficients for training goal of maintaining.

| AC | reference WTL coefficient | Offset | WTL coefficient, easy | WTL coefficient, moderate | WTL coefficient, hard |
|---|---|---|---|---|---|
| 4-8 | 3.3 | 0.5 | 2.8 | 3.3 | 3.8 |

TABLE 2 weekly training load coefficients for training goal of increasing.

| AC | reference WTL coefficient | Offset | WTL coefficient, easy | WTL coefficient, moderate | WTL coefficient, hard |
|---|---|---|---|---|---|
| 4-8 | 3.6 | 0.6 | 3.0 | 3.6 | 4.2 |

TABLE 3 weekly training load coefficients for training goal of increasing fast.

| AC | reference WTL coefficient | Offset | WTL coefficient, easy | WTL coefficient, moderate | WTL coefficient, hard |
|---|---|---|---|---|---|
| 4-8 | 3.8 | 0.4 | 3.4 | 3.8 | 4.2 |

The tables 1-3 show that the WTL coefficient for a moderate block corresponds to the reference WTL coefficient value, while an easy block includes the reference WTL coefficient value subtracted by the offset value and a hard block includes the reference WTL coefficient value added with the offset value. In tables 1-3, same WTL coefficient and offset values have been used for all activity classes (4-8). In an alternative, separate reference WTL coefficient values and offset values may be used with each AC. In addition, the three WTL coefficient values given for easy, moderate and hard blocks may be unevenly spaced. For example, if two offset values are used, one of those may be used for decreasing the reference WTL coefficient and the other for increasing it.

The realized weekly training load coefficient (or its integer part 1-5) may also be called the relative weekly training load. In FIG. 5 and tables 1-3 week or weekly may be replaced by n-number of days, e.g. for training load and training load coefficient. In such case, also the other values, percentages and/or constants may be adjusted.

Training load may be set in a scale according to a cumulative physiological quantity, which may be a linear quantity. An example of cumulative physiological quantity is EPOC, which may be scaled linearly to a training effect (TE), which is dependent on the present activity class of the user. Training load may be estimated by at least one quantity of heart rate, speed, time, distance and/or power output, which is describing the total physical load of workout.

FIG. 6 illustrates a decision tree. A decision tree may be used for providing a current next workout recommendation, for a day, as a percentage of the weekly training load. The previous workout data, from training history data, comprises at least two past detected workouts, which may be from the past two days or, if the user has performed training today, from today and yesterday. The realized training load values (X) of the previous workout(s) are detected and determined as a percentage of the weekly training load target, % WTL-X. The weekly training load target, WTL-X may be determined based on the WTL coefficient value and the present activity class of the user, e.g. as illustrated in FIG. 5, and it represents the absolute weekly training load value, which will be accumulated on average over each seven-day period, if the present block is continued indefinitely. The detected previous training load values, of the two previous trainings, e.g. from yesterday and the day before yesterday, are compared to the training load target of the training block WTL-X in order to get percentages for the previous trainings. The percentages for today, yesterday and the day before are calculated relative to the present weekly training load target of the present block corresponding to the present target training load coefficient value of the block. The target weekly training load coefficient value of the present block may be added/subtracted with an offset value in the case of an easy/hard block, correspondingly.

FIG. 6 illustrates phases shown on left and separated by dashed lines. First, previous training session is evaluated in order to establish the previous performed training being as none, light or maintain/increase level of training. A decision tree of FIG. 6 determines how to proceed based on the established level of the previous training session. Next, a training session from a day before the evaluated previous training session may be evaluated. The training session may have been maintain or increase, as illustrated in FIG. 6. Based on the previous selections according to the decision tree of FIG. 6, present realized WTL coefficient may be taken into account. In the FIG. 6, % WTL-X is calculated relative to the target weekly training load value, which is calculated using the present WTL coefficient. Next, NWR candidate may be determined. The NWR candidate is presented as a training load peak value for the current NWR candidate, as percentage of WTL target. After NWR candidate has been determined, a recovery time may be taken into account. After this, final NWR is provided, as a percentage of the WTL target, leading to light/recovery, maintain/recovery or maintain/increase level of the NWR.

Preselected selection rules are determined in order to compare the calculated percentage values to a predetermined limits. In top phase of FIG. 6, taking into account previous training session, sum of training loads is determined for today or yesterday including previous daily workout/training sessions, and the sum is divided by the training load target of the present block, thus forming a percentage value % WTL-X. The training load target is dependent on the activity class. Each activity class has its own, specific training load target(s). If the % WTL-X of previous training, is over a predetermined percentage, the user has performed a workout for maintaining or improving. In this case the previous workout is determined to be maintain or improve. According to the decision tree of FIG. 6 the following NWR shall be recovery and the decision tree continues from maintain/increase to a recovery time phase, via which a recovery time may be taken into account for providing next NWR. The NWR candidate for the next recommended workout is in this case represented by the value L1 in FIG. 6.

The aforementioned predetermined percentage for a previous training session phase evaluation may be 4-10%, or 5-8%, for example. The NWR candidate for the light exercise may get a value in the range of 0-8%, for example.

If at the phase of previous training session, previous % WTL-X is below the predetermined percentage, the user has performed previously a light or a very light workout. In this case, the decision tree continues to day before previous training session phase, where a sum of training loads is determined for the day before the previous training session and divided by the training load target of the present block in order to form a percentage value for the day before previous training session % WTL-X, which is then taken into consideration. % WTL-X is calculated as sum of training load for a day divided by WTL target of the block.

If at the phase of previous training session, the detected % WTL-X of the previous (daily) training session is below the predetermined percentage and over zero, it is determined that the user has performed a (very) light training session.

Then, the decision tree of FIG. 6 continues to the phase of day before previous training session, where a sum of training loads for a day before the previous training session is calculated and divided by WTL target of the block. If the detected % WTL-X of the day before the previous training session is above a predetermined percentage, it corresponds to training session for improving. Thus, the day before the previous training session is determined to correspond to improving training session, after the previous training being (very) light. The following NWR is determined to be maintain. Next, present weekly training load coefficient is taken into account for creating NWR candidates. Levels of maintaining M2, M3, M4 are determined for different integer parts—1, 2 and 3-5, correspondingly—of the realized weekly training load coefficient calculated using the realized weekly training load sum summed over the past seven days. The aforementioned integer part may be determined using FIG. 5 as the zone (between 1-5), where the realized weekly training load is located at the location of the horizontal x-axis determined by the present activity class of the user, M2, M3, M4 illustrate initial percentages or candidates for NWR. The percentages of M2, M3 and M4 may be 15-30%, such that the value of M2 is bigger than the value of M3, which is bigger than the value of M4.

The predetermined percentage for a day before the previous training session phase evaluation may be 15-30%, or 20-25%, for example.

If the detected % WTL-X of the day before the previous training session is below a predetermined percentage, it corresponds to maintaining or low intensity training, or rest. The following NWR is determined to be an improving training. Next, the integer part of the weekly training load coefficient calculated with the realized weekly training load sum is again taken into account. Levels of improving I1, I2, I3 are determined for each integer part of the realized weekly training load coefficient correspondingly. I1, I2 and I3 illustrate initial percentages or candidates for NWR. The percentages of I1, I2 and I3 may be 35-45%, such that the value of I1 is bigger than the value of I2, which is bigger than the value of I3. For the integer values 4-5 of the realized weekly training load coefficient, the initial percentage or candidate for NWR is determined to be M1. M1 may be 15-30%, such that M1 has bigger value compared to value of M2.

If the detected % WTL-X of the previous training session illustrates that the user has performed no training/exercise, for example the percentage is zero, % WTL-X of the day before the previous session is detected. If the detected % WTL-X for the day before the previous session is less than a predetermined percentage, that training session corresponds to a maintaining or low intensity training, or rest. Thus, the following NWR is to improve. Next, the integer part (in the range of 1-5) of the realized weekly training load is again determined. For the integer value of 1, the NWR is percentage of I1 of WTL-X; for the integer value of 2, the NWR is percentage I2 of WTL-X; for the integer value of 3, the NWR is percentage I3 of WTL-X; for the integer values of 4-5, the NWR is percentage M1 of WTL-X.

If the detected % WTL-X of the previous training session illustrates that the user has performed no training/exercise, for example the percentage is zero, % WTL-X of the day before the previous session is detected. If the detected % WTL-X for the day before the previous session is above a predetermined percentage, that training session corresponds to improving. Thus, the following NWR is to maintain. Next, the integer part (in the range of 1-5) of the realized weekly training load coefficient is again determined. For the integer value of 1, the NWR is percentage of M2 of WTL-X; for the integer value of 2, the NWR is percentage M3 of WTL-X; for the integer values of 3-5, the NWR is percentage M4 of WTL-X.

When NWR candidates are determined according to FIG. 6, the determination(s) may comprise adding or subtracting a predetermined constant(s). When NWR candidates are determined according to FIG. 6, the determinations may comprise adding or subtracting constant values from the NWR candidates. For example, a small positive constant may be subtracted from the NWR candidates, if the previous training session was light.

In addition to the rhythm of training, or phase of micro-cycle and/or meso-cycle, of past two training sessions, the total accumulated fatigue is taken into account when providing the NWR. Even though last training session would have been easy training, which is typically followed by a harder training session, easier training is recommended if total weekly load sum, corresponding to cumulative fatigue, is high. On the other hand, if both WTL and last training sessions show that training has been very easy/light, then the user is recommended to do a relatively hard training session to catch up weekly goals.

If the detected % WTL-X of previous (daily) session is determined being (very) light and if the detected % WTL-X of the day before the previous session determined to be at low or maintaining level, the following NWR is planned for a high-intensity exercise, i.e. increasing the fitness level. The integer part (in the range of 1-5) of the realized weekly training load coefficient is again determined. When the integer part is between 1-3, the NWR candidate or initial percentage is determined via percentages I1, I2, I3 correspondingly, as shown in FIG. 6. For the integer part values 4-5, the NWR candidate is determined by utilizing percentage M1.

The training load peak value for the current next recommended workout may be obtained via multiplying the weekly training load WTL target value of the present block by the final percentage value.

Optionally, a recovery time may be taken into account, as the following phase of the decision tree of FIG. 6. The recovery time may be calculated/determined after every training session. The higher the training effect values, the higher may be the recovery times. Predetermined ranges T1, T2, T3 of recovery time may have effect on NWR determination/updating. The recovery time(s) may be determined in days or hours. A threshold value may be set for the recovery time(s). For example, recovery time may be 24-68 hours, such that value of T1 is smaller compared to T2, which is smaller compared to T3. The values T1, T2, T3 may comprise ranges instead of single values. If recovery time is for example between 24 and 60 hours, this may correspond to T2 and the following NWR is downgraded to recovery (rest or light training) from maintain; or to maintain from improve. The training load of NWR candidate may be limited to a specific level such that NWR corresponds to maintain or recovery. Alternatively previously determined NWR candidate may be used as final NWR. If a recovery time is T1 (small), no changes are made to an NWR candidate. When recovery time has been long, e.g. over a threshold of T3, light exercise or recovery session is recommended as NWR.

Parameters of FIG. 6 relating to a week, like WTL, WTL target, may be replaced by n-number of days instead of the 7-day week. This may involve adjusting other values, percentages and/or constants, as presented. For example, WTL may be replaced by a training load for n-days, which is calculated as a sum of training load peak values from today and (n+1) previous days. WTL target may be replaced by training load target for n-days, which is then compared to sum of n realized training load values, or to training load peak value(s) for current NWR candidate(s) or NWR(s).

Utilizing estimated recovery time may be useful in a case when last few days have comprised easy training and there is a very hard session e.g. three days ago. For example, the user has completed an endurance running race in the evening of the day one, done a base endurance run of 20% WTL-X of the day two and rested the day three. According to literature, an endurance running race (of the day one) may cause up to 96 hours of recovery need. The base endurance running race of the following day two, increases the accumulative recovery time. In the morning after the three days, on day four, the user may have WTL coefficient of 3.8, while the user may have recovery time of T2. Thus, in accordance to the recovery time T2 of FIG. 6, the NWR would yield to recovery. The candidate NWR is limited to a certain predetermined percentage, e.g 10-25%, of the target WTL. If the recovery time is not taken into account, the NWR candidate might yield to NWR with e.g. 40% of the target WTL. Reduction percentage may be variable based on a present determined activity class or purpose of the training plan. Training plans that are aimed to increase fitness faster may have a lower reduction percentage.

Publication U.S.2016184637 presents ways to determine recovery time(s) from freely performed exercise data. Such may be utilized for determining recovery times, as illustrated in FIG. 6.

In addition, HRV based readiness level or user feedback on readiness may have an effect on the choice between using the calculated NWR candidate or the final NWR. For example, if HRV values during a day are significantly below user's normal level or if user feedback provides indication of significantly increased perceived fatigue, these parameters may be used similarly as recovery time. Lower readiness may be used to downgrade the initial NWR candidate.

Duration for the current exercise may be selected based on the determined present activity class, the present block (being easy, moderate or hard), and the training goal (being improving, improving fast or maintaining) and the corresponding training intensity. Finally, intensity of the exercise, heart rate limits, speed of the exercise and/or distance are determined. The determinations of intensity, heart rate limits, speed and distance may be carried out via a simulation at a constant intensity. The simulation may calculate EPOC and TRIMP curves, and the training load peak curve, for several intensity levels for the training of the given duration. Optimal intensity value may be determined using a binary search and an intensity range may be given as an optimal intensity (percentage) with some approximation, e.g. ±3-10%. The simulation utilizes fitness level, the target training load peak value, the duration of the workout, and maxHR of the user. The heart rate range and speed of exercise may be determined via linear transformation from the intensity range. The distance may be linearly estimated from the duration and mean speed. An average running speed range may be estimated from the determined intensity range via linear transformation: speed=a+b*intensity.

An adaptive training coach is provided. In addition to the training load and schedule, the adaptive training coach may provide proposals with a certain form(s) of physical activity. The adaptive training coach may provide alternative proposals for form(s) of training and exercises. A training plan is automatically generated. The training plan is based on a training goal and exercise intentions of a user. Thus, a user may input desired exercises or form(s) of physical activity, or those may be taken into account from training history data of previous exercises in order to generate the training plan. Adaptation of the training plan may include matching the training goal/generated plan with training intentions. For example, if based on history data a user is able to achieve targets by performing certain trainings, like running, skiing, floorball or badminton, these may be recommended accordingly. If easy exercise is planned, harder workouts may not be proposed, but e.g. Nordic skiing is suggested instead for an easy training session. Adaptation may be done daily, after each detected/saved workout, weekly, once or twice at a training block, or at other intervals. For example an estimated recovery time, if over a predetermined value, may trigger adaptation. In addition or alternatively, workouts performed in a different order compared to the training plan/NWR may trigger adaptation. The adaptation is based on a decision tree, which enables adapting and modifying the training plan and next workout recommendation(s) according to user's actual, realized weekly training load and previous trainings as performed. The decision tree may be based primarily on a training load. The adaptive training coach is easy for a user to adjust: user may take a day off or make a harder or easier workout than recommended (NWR). The adaptive training coach takes user performed workout into account, when generating a training plan and/or a next workout recommendation (NWR).

In addition to adapting and updating the training plan based on saved and/or monitored previous workout exercises, the adaptive training coach may provide variety to the training plan, i.e. different exercises, intensities, durations of exercises, and so on, for achieving the set training goal. The training goal relates to physiological goal of a user, which may relate to a certain activity class. Next workout recommendation (NWR) may be based on percentage of a total training load (value) of a training block. A single next workout recommendation may be generated at a time. There is no need to accomplish calculations for future workout recommendations, thus unnecessary repeating calculations may be unnecessary and/or avoided.

In order to convert the recommended training load of the NWR into a variety of recommendations, further calculations may be accomplished. Variety of recommendations may be based on user specified type(s) of preferred workout(s) or exercise(s) or other user specified parameters, like intensity or time of exercise. Log of previous workouts or workout history data may be scanned. Based on workout history data, a workout that is found to be approximately in the range of the target training load is recommended. Based on workout history data a training effect approximation may be made. For example, calculating that while running at certain speed for an hour, the user produced a certain TRIMP value. Correspondingly, time and speed for the next exercise, presented in the NWR, is determined. Alternatively or in addition, a route with a specific time may be suggested as a NWR. One variable of NWR may be based on combination of training effect TE and training status. Training status may be determined as presented in U.S.2018174685. For example, training status may be negative, such as unproductive, where training seems ok, but fitness decreases for some reason. As fitness decrease may be caused by illness or excessive stress, unproductive status occurs in situations where body may struggle with recovery. Therefore such negative statuses may be used to downgrade NWR candidate. Similar downgrading logic may be applied in overreaching status, which is due to too high training load making the training counterproductive. In addition contextual feedback relating to NWR value and type of workout recommended may be provided. For example, additional guidance may comprise instructions to a user in order to achieve a particular cumulative physiological goal (value). This may include instructions for performing a relatively short workout that includes short, high-intensity intervals; or instruction relating to amount of ratio of aerobic to anaerobic exercise.

User may be presented with various potential training plans or programs. A training plan may comprise training schedules with recommended training load values. The training plans may be represented by a description of a goal of a particular training plan. The description may be: maintain, increase/boost, or increase fast/boost fast a fitness level of a user. The different difficulty levels may be defined by an intensity (amount of training load), a number of rest days, a present activity class, a target final activity class or other variables. Each activity class have their own target training load and offset value.

A training goal of maintaining an exercise level need not exceed its training load from block-to-block. The training goal of maintaining a fitness level has lower load targets for each different training block (e.g. week) compared to a training goal of increasing fitness level. Different training blocks may comprise easy, moderate and hard training blocks, which differ in their load targets. The training goal of maintaining a fitness level may be based on exercise intensity of a user, for example it may relate to a user's maximum oxygen consumption VO2max capacity and/or maximum metabolic equivalent maxMET, as a measure of exercise intensity. A training goal of maintaining a fitness level enables maintaining the fitness level of a user and difficulty of training regardless of possible deviations from recommended workouts. For example, a user may occasionally train more frequently than planned in maintain mode, where NWR system may not follow monthly training load as it would in improve mode. Instead, in maintain mode the system may follow only user's fitness level and select the training load accordingly. On the contrary, in improve mode system tracks also monthly training load and may update training plan towards more difficult even with similar training history, if monthly training load has exceeded a threshold value although VO2max had not.

If a training goal is to increase exercise level, the training load is increased progressively. A training goal may comprise increasing/boosting a particular aspect of fitness. The particular aspect may be aerobic/anaerobic, for example. The training plan may then utilize training effect calculations related to proportion of aerobic to anaerobic exercise of a workout, e.g. as described in publication U.S.2017143262.

A user may set a period for achieving the training goal, e.g. a date of a competition. The training plan is divided into blocks/periods, for which training load may be distributed differently. Thus the training plan may comprise blocks of different sub-goals and sub-target loads. For a short period of time, which may be based on set target time, e.g. on upcoming event, a peaking program may be generated. Few or single training block(s) may be generated with an aim to give a final additional boost in fitness prior to a target time/event, like a competition. A peaking program for providing a final additional boost may be generated to maintain or reduce training load, e.g. by reducing training volume, while maintaining high training intensity.

Training blocks may represent different kinds of training, like easy/medium/hard. This corresponds to an actual coach by planning variation of weeks among harder and easier weeks. With variate training blocks workout targets, training duration and intensity are flexibly adjustable. In addition, it enables adjusting the purpose of each training block depending on the number of rest days or easy training days the user chooses to make. In case a user takes easier training days than planned, for example including less training load or intensity than recommended, the training block may be adjusted by replacing the present block with another block that suits better with the monitored exercises of the user. In addition or alternatively, each block may be adjusted by adding or subtracting a certain amount of training load from the target training load. An offset value, being added to/subtracted from the target weekly training load coefficient, may be used to increase/decrease the recommended training load, e.g. increase for hard week; decrease for easy one. An activity class may have an effect on the offset value. For example, more experienced athletes having higher activity class may be able to handle higher variation in training load compared to user having lower activity class. A training goal may have effect on offset value. For example, goal of improving fast has higher weekly load target and relatively lower offset value compared to goal of maintaining fitness level. The offset value provides amount for flexibility and possible change in values, while still maintaining the set goal.

The adaptivity may be based on a decision tree and predefined selection rules. The predefined selection rules may comprise contextual logic rules, as part of a software product. The predefined selection rules may utilize offset value(s) and achieve appropriate training loads for appropriate days. A training plan may vary among offset value. Especially training plan and next workout recommendation(s) may be adjusted by offset value. This provides variety to training plan, while still enabling achieving the set training goal. For example, the offset value may be added to a training load or time (of NWR), when it is recognized that during weekends or holidays user may have more time available for a longer or harder workout. In another example, the offset value may be subtracted from a training load or time (of NWR), if a potential fatigue state of a user is recognized, e.g. as a result of a recent very high intensity workout. If daily activity monitoring is done and it is recognized that a user has been more active than normal, intensity of planned workout may be reduced by the offset value. A user may prefer to rest or to do light training; or to do a hard or a long training. In this case, the offset may be used for adjusting the training block accordingly.

Next workout recommendation (NWR) may be provided in different formats. NWR may include some form of quantifiable variable. NWR may include a target cumulative training effect score, which may relate to EPOC, TRIMP, distance/power measure as function of time (e.g. speed), cumulative amount of energy expenditure over time, specific route to travel within a set time, or some other suitable parameter. In an example next workout recommendation is presented as, or represented by, a recommended training effect score. NWR may include a NWR specification figure, where training load of a training block is placed within training effect ranges. NWR may be presented as scaled in the form of a cumulative physiological measure, e.g. training effect, EPOC or TRIMP. Using percentage of WTL target as a workout target enables automatic training planning regardless of the used cumulative quantifiable training load score.

The adaptive training coach, as presented in this application, enables adjusting target training load such that the training plan and NWRs remain reasonable, despite the changes/updates made. The training load target for a training block is adjustable within an acceptable range, which may be determined by an offset value, such that the set goal of the block is not compromised, or at least maintain exercise level of training is enabled. An unreasonable hard or easy workout is not recommended. For example, if last week is detected being exercised at lower level than planned, a target load of the next workout recommendation is increased a bit, within determined offset value. As an example, initially generated training plan/NWR comprising 40% of weekly training load, may be extended up to 42% of weekly training load, if past training shows too low for achieving the set goal/target training load. Nothing dramatic is recommended even if a whole week/block is detected without any exercise. In known systems a target training load goal for a week may be determined and divided by number of days. In case of a non-planned day off or moderate training compared of planned, many systems simply redistribute the remaining training load over the remaining days. This can yield to unreasonable training load recommendations.

The presented adaptive training coach requires no predefined templates, nor storage for such. Instead a decision tree and predefined selection rules are utilized. This provides additional flexibility for adapting the training plan and parts of it. Less processing resources and time is required for implementation compared to one(s) with training template banks, which include large amount of data. This makes the adaptive training coach suitable for compact devices. No external devices, memory, database, server or processing is required for providing NWR(s).

Figure 7:
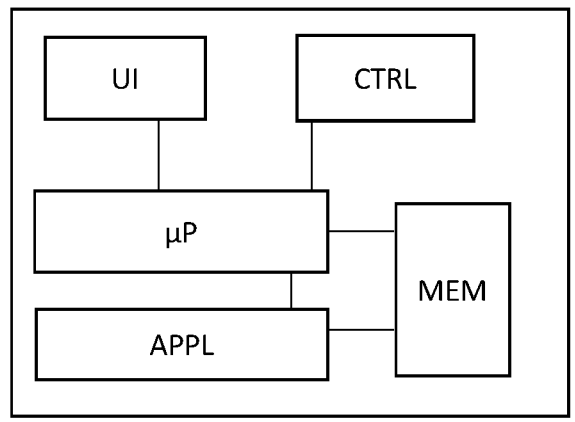
FIG. 7 is a non-limiting block-diagram illustrating an apparatus according to an embodiment.

FIG. 7 illustrates an apparatus for providing an adaptive training coach. FIG. 7 shows a simplified block diagram of the apparatus. The apparatus comprises a module APPL, at least one processor µP, at least one memory MEM and a user interface module UI. The at least one memory MEM is configured to store or record information and executable instructions. The module APPL comprises modules, for example executable instructions, configured to determine a training program, NWR and variables. The module APPL may include, for example, executable instructions configured to access and/or receive user background information, executable instructions configured to determine a present activity class, executable instructions configured to calculate/compare variables, executable instructions configured to determine and/or update a monthly training load, executable instructions configured to determine and/or update a weekly training load, executable instructions configured to determine a phase of a micro-cycle of workouts and/or meso-cycle of blocks, executable instructions configured to generate and/or provide a training plan, executable instruction configured to provide a next workout out recommendation (NWR), executable instructions configured to access and/or process and/or add training history data, executable instructions configured to determine weekly training load sum, executable instructions configured to calculate light fraction, executable instructions configured to get an initial percentage, executable instructions configured to determine a training load target for a workout and/or executable instructions configured to determine recovery time, for example as illustrated in FIGS. 1-6. A user interface UI is configured to receive information inputted by a user and to present information. The user interface UI may be used to receive inputted information, like user background information and/or to present information, like presenting training plan information or a next workout recommendation(s) to a user.

Various embodiments of at least one memory MEM may include any suitable data storage technology type, including but not limited to semiconductor based memory devices, magnetic memory devices and systems, optical memory devices and systems, fixed memory, removable memory, disc memory, flash memory, non-transitory computer readable memory, dynamic random access memory (DRAM), static random access memory (SRAM), electrically erasable programmable read-only memory (EEPROM) and the like.

Various embodiments of the processor μP include, but are not limited to, general purpose computers, special purpose computers, microprocessors, digital signal processors (DSPs) and multi-core processors.

The apparatus of FIG. 7 may comprise a processor μP and computer executable instructions stored in a memory MEM, which are arranged to determine and update one/more next workout recommendation(s). The apparatus of FIG. 7 may comprise a hardware, like an electric circuit, an application specific integrated circuit (ASIC), a field-programmable gate arrays (FPGA), a microprocessor coupled with memory that stores instructions executable by the microprocessor.

The apparatus of FIG. 7 may comprise a controller CTRL, or a heart rate module, configured to receive a signal from a pulse sensor or a heart rate sensor. The module APPL may be configured to process the received signal, with aid of the microprocessor μP and data stored/recorded to the memory MEM.

The module APPL of FIG. 7 is configured to process data, for example as illustrated in FIGS. 1-6. The module APPL may be implemented as a computer logic, a software and/or a computer program stored in a memory, for example to the at least one memory MEM.

Figure 8:
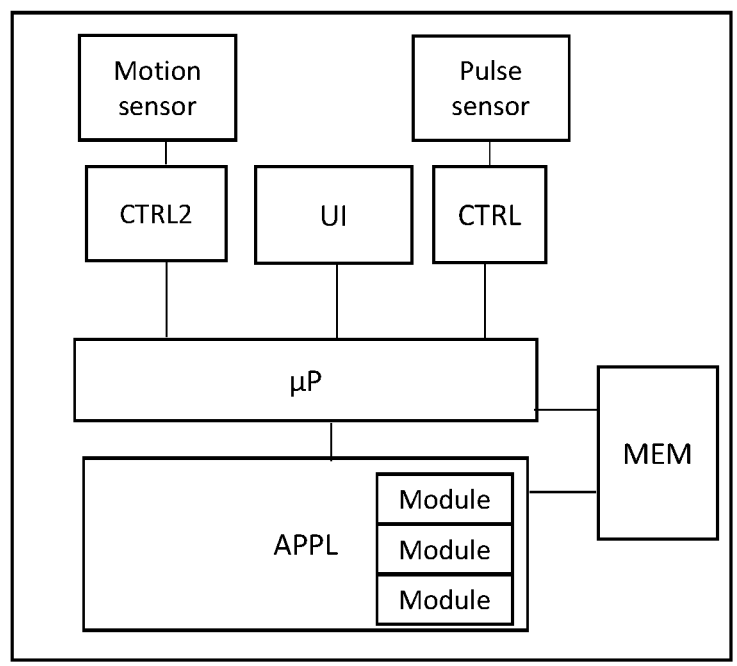
FIG. 8 is a non-limiting block-diagram illustrating an apparatus according to an embodiment.

In addition to modules presented in FIG. 7, FIG. 8 illustrates a controller CTRL2, a pulse sensor and a motion sensor configured to provide signals to corresponding controllers CTRL, CTRL2, and modules of APPL.

The apparatus of FIG. 8 may comprise a controller CTRL, or a heart rate module, configured to receive a signal from a pulse sensor or a heart rate sensor. The pulse sensor may be arranged in contact with, attached to, a user. An apparatus configured to monitor heart rate may comprise a monitor device, a heart rate monitor, a pulse rate monitor, a biometric device, a personal monitor, a portable monitor or a wearable monitor. Heart rate (HR) may be monitored using a monitor or a monitor device, like an electrocardiogram (ECG), a photoplethysmogram (PPG), a portable or a wearable monitor, e.g. a wrist top, or alike. The apparatus may comprise a physiological sensor, like an optical reflectometer. The apparatus, like a heart rate monitor, enables measuring and/or monitoring heart rate of a user and providing the measured signal(s) to a controller CTRL or a heart rate module.

The apparatus of FIG. 8 may comprise a controller CTRL2, or a motion data module, configured to receive a signal from a motion sensor. The motion sensor is arranged to sense motion data of the apparatus or a user wearing it. Motion data may comprise position data, movement data and/or change in position. An apparatus configured to monitor position may comprise a monitor device. A monitor may comprise a global positioning system (GPS), an accelerometer, a gyroscope, a power meter or alike position determination system. At least some parameters may be inputted by a user after the exercise, The apparatus, like a motion monitor, enables measuring and/or monitoring movement and/or position of a user and providing the measured signal(s) to a controller CTRL2.

All or selected modules of the apparatus of FIG. 8 may be implemented using an integral circuit, for example an application specific integrated circuit (ASIC).

In addition, apparatus of FIGS. 7 and/or 8 may comprise means for accessing a remote or external server, memory, device, database, data processing capacity or alike source, for providing information related to any of phases as illustrated in FIGS. 1-6. For example, a centralized server may include training history data and/or be used for calculating or determining parameters, constants and/or variables for the phases. For example, updates for determinations may be provided via accessible data source centrally.

Unless otherwise defined, technical and scientific terms used herein have the same meaning as is commonly understood by one having ordinary skill in the art to which this disclosure belongs. The terms "first", "second", and the like, as used herein do not denote any order, quantity, or importance, but rather are employed to distinguish one element from another. Also, the terms "a" and "an" do not denote a limitation of quantity, but rather denote the presence of at least one of the referenced items. The use of "including", "comprising" or "having" and variations thereof herein are meant to encompass the items listed thereafter and equivalents thereof, as well as additional items. The terms "including", "comprising" or "having" and variations thereof inherently consist of the items listed thereafter and equivalents thereof. The terms "connected" and "coupled" are not restricted to physical or mechanical connections or couplings, and may can include electrical or optical connections or couplings, whether direct or indirect.

Furthermore, the skilled artisan will recognize the interchangeability of various features or parts from different embodiments. The various features or parts described, as well as other known equivalents for each feature, can be mixed and matched by one of ordinary skill in this art, to construct additional systems and techniques in accordance with principles of this disclosure.

In describing alternate embodiments of the apparatus claimed, specific terminology is employed for the sake of clarity. The invention, however, it is not intended to be limited to the specific terminology so selected. Thus, it is to be understood that each specific element includes all technical equivalents that operate in the same or similar manner to accomplish the same or similar functions.

It is to be understood that the foregoing description is intended to illustrate and not to limit the scope of the invention, which is defined by the scope of the appended claims. Other embodiments are within the scope of the following claims. It is noted that various non-limiting embodiments described and claimed herein may be used separately, combined or selectively combined for specific applications. Further, some of the various features or parts of the above non-limiting embodiments may be used to advantage, without the corresponding use of other described features. The foregoing description should therefore be considered as merely illustrative of the principles, teachings and embodiments of this invention, and not in limitation thereof.

The invention claimed is:

1. A method for providing a next workout recommendation (NWR) comprising:
   determining, by a processor, a present activity class of a user, which corresponds to a present fitness level of the user;
   receiving, by the processor, a training goal of the user, which relates to maintaining or increasing the present fitness level of the user;

determining, by the processor, a total target training load based on the present activity class and the training goal;

detecting, by the processor, a sum of training load values for n-days from training history data, wherein n is an integer representing n-number of successive previous daily training session(s);

detecting, by the processor, realized training load value(s) for performed daily training session(s) of at least one day from the training history data;

determining, by the processor, a phase of a micro-cycle of successive training days for the next workout recommendation (NWR) by the realized training load value(s) for performed daily training sessions(s) of the at least one day, as a percentage of the sum of the training load values for n-days;

determining, by the processor, a current training load target for the next workout recommendation (NWR) based on the present activity class, the determined phase of the micro-cycle and the sum of the training load values for n-days; and providing, by the processor, the next workout recommendation (NWR) for the following workout based on the current training load target determined for the NWR.

2. The method according to claim 1, further comprising adding the provided NWR to the training history data and repeating to provide a following NWR(s) taking into account a provided, but not yet performed, NWR(s) in order to form a training plan comprising two or more following NWRs.

3. The method according to claim 1, wherein the micro-cycle of successive training days comprises at least training days of rest, maintain and improve; and wherein the NWR comprises one of rest, maintain and improve.

4. The method according to claim 1, wherein a training day comprises a sum of training load values of performed daily training(s).

5. The method according to claim 1, wherein the sum of the training load values for n-days comprises a sum of training load values from the current day and (n-1) previous days, wherein n is in a range between 4 and 12.

6. The method according to claim 1, further comprising dividing the total target training load into a meso-cycle of training blocks, wherein the meso-cycle comprises successive training blocks of different training load targets, and wherein each training block comprises one or more micro-cycle(s), wherein each micro-cycle comprises one or more days;

determining a phase of the meso-cycle of the training blocks by detecting location(s) of micro-cycle(s) via the detected realized training load values of performed daily training session(s) of at least two days; and comparing the detected realized training load values from the two days with the sum of the training load values for n-days, which is associated with the blocks of different training load targets at the present activity class.

7. The method according to claim 6, wherein the meso-cycle comprises easy, moderate and hard training blocks; wherein a target training load of a moderate block is set as a reference training load;

a target training load of the easy training block is determined by the reference training load subtracted by an offset value; and a target training load of the hard training block is determined by the reference training load added by the same or a different offset value.

8. The method according to claim 7, wherein offset value(s) are determined for each present activity class.

9. The method according to claim 1, wherein the present activity class is determined based on at least one of:

the present fitness level;

a training load of m-days, wherein m is an integer in a range between 24 and 38, representing m-number of successive previous daily training session(s);

a maximum aerobic capacity, a maximum metabolic equivalent, a maximum oxygen consumption, and the larger of the present fitness level and an activity class determined via a training load of previous m-days, wherein m is an integer in a range between 24 and 38, representing m-number of successive previous daily training session(s).

10. The method according to claim 1, further comprising taking into consideration the realized training load values from the day n-2, if the detected realized training load value from the day n-1 falls below a predetermined value.

11. A method according to claim 1, further comprising determining an NWR candidate as a ratio between a target training load for the next workout recommendation and a target training load of the block, based on a training load coefficient dependent on a training load of the block.

12. The method according to claim 11, further comprising determining a recovery time from at least one of: a past training and between past previous successive trainings; and adjusting the NWR candidate based on the determined recovery time.

13. The method according to claim 1, wherein the next workout recommendation (NWR) comprises at least one or more of:

a training load target, a target training effect, duration, phase, distance, intensity limits, heart rate limits and/or speed limits for the NWR, a target distance or intensity as a function of time, a target cumulative amount of energy expenditure over time, a target route to take within a set time, and workout guidelines based on previous workouts performed by the user.

14. The method according to claim 1, further comprising taking into account a training history data of a predefined or existing number of workout(s) performed by the user, the training history data comprising at least one or more of the following for each previous day(s):

date and time information, wherein the time information comprises the time of ending the training at the previous day(s), a training load, a recovery time from the previous workout or between the successive previous workouts, a maximum metabolic equivalent (maxMET) of the user, a maximum oxygen consumption (VO2max) capacity of the user, and a type of a workout.

15. The method according to claim 1, further comprising adjusting a target training load of the NWR based on a sum of training load peak value(s) from at least one or two previous day(s) of the training history data.

16. The method according to claim 1, further comprising a decision tree for providing a next workout recommendation(s).

17. An apparatus for providing a next workout recommendation, the apparatus comprising:
- a processor configured to determine a present activity class of a user, which corresponds to a present fitness level of the user,
- the processor configured to receive a training goal of the user, which relates to maintaining or increasing the present fitness level of the user;
- the processor configured to determine a total target training load based on the present activity class and the training goal;
- the processor configured to detect a sum of training load values for n-days from training history data, wherein n is an integer representing n-number of successive previous daily training session(s);
- the processor configured to detect a sum of training load values for n-days from training history data, wherein n is an integer representing n-number of successive previous daily training session(s);
- the processor configured to detect realized training load value(s) for performed daily training session(s) of at least one day from the training history data;
- determining a phase of a micro-cycle of successive training days for the next workout recommendation (NWR) by the realized training load value(s) for performed daily training sessions(s) of the at least one day, as a percentage of the sum of the training load values for n-days;
- the processor configured to determine a current training load target for the next workout recommendation (NWR) based on the present activity class, the determined phase of the micro-cycle and the sum of the training load values for n-days, and
- the processor configured to provide the next workout recommendation (NWR) for the following workout based on the current training load target determined for the NWR.

18. The apparatus according to claim 17, further comprising a decision tree for providing a next workout recommendation(s) (NWR).

19. The apparatus according to claim 17, wherein the processor is configured to add the provided NWR to the training history data, and wherein the provided NWR is taken into account to provided a subsequent NWR.

20. A non-transitory computer program product for providing a next workout recommendation comprising executable instructions, which when executed by a processor, are arranged to:
- determine a present activity class of a user, which corresponds to a present fitness level of the user;
- receive a training goal of the user, which relates to maintaining or increasing the present fitness level of the user;
- determine a total target training load based on the present activity class and the training goal;
- detect a sum of training load values for n-days from training history data, wherein n is an integer representing n-number of successive previous daily training session(s);
- detect realized training load value(s) for performed daily training session(s) of at least one day from the training history data;
- determine a phase of a micro-cycle of successive training days for the next workout recommendation (NWR) by the realized training load value(s) for performed daily training sessions(s) of the at least one day, as a percentage of the sum of the training load values for n-days;
- determine a current training load target for the next workout recommendation (NWR) based on the present activity class, the determined phase of the micro-cycle and the sum of the training load values for n-days; and
- provide the next workout recommendation (NWR) for the following workout based on the current training load target determined for the NWR.

* * * * *